United States Patent
Hou et al.

(10) Patent No.: US 10,463,308 B2
(45) Date of Patent: Nov. 5, 2019

(54) LOWER LIMB SPASTICITY MEASUREMENT METHOD

(71) Applicant: HIWIN TECHNOLOGIES CORP., Taichung (TW)

(72) Inventors: Jung-Fu Hou, Taichung (TW); Yu-Chia Liang, Taichung (TW); Chang-Jin Yu, Taichung (TW)

(73) Assignee: Hiwin Technologies Corp., Taichung (TW)

( * ) Notice: Subject to any disclaimer, the term of this patent is extended or adjusted under 35 U.S.C. 154(b) by 277 days.

(21) Appl. No.: 15/167,511

(22) Filed: May 27, 2016

(65) Prior Publication Data

US 2017/0340286 A1    Nov. 30, 2017

(51) Int. Cl.
*A61B 5/11* (2006.01)
*A61B 5/00* (2006.01)

(52) U.S. Cl.
CPC .............. *A61B 5/702* (2013.01); *A61B 5/112* (2013.01); *A61B 5/1107* (2013.01);
(Continued)

(58) Field of Classification Search
CPC .......... A61H 1/00; A61H 1/02; A61H 1/0237; A61H 1/0262; A61H 1/024; A61H 1/0244; A61H 3/00; A61H 3/008; A61H 2003/007; A61H 2201/0107; A61H 2201/0157; A61H 2201/12–123; A61H 2201/1673;
(Continued)

(56) References Cited

U.S. PATENT DOCUMENTS 5,052,406 A * 10/1991 Nashner ............... A61B 5/0488 600/595
6,589,190 B2 * 7/2003 Kanderian, Jr. ...... A61B 5/0488 600/587
(Continued)

FOREIGN PATENT DOCUMENTS

AT        508091 A1    10/2010

OTHER PUBLICATIONS

Banala, et al. "A powered leg orthosis for gait rehabilitation of motor-impaired patients." Robotics and Automation, 2007 IEEE International Conference on. IEEE, 2007.*
(Continued)

*Primary Examiner* — David J. McCrosky
(74) *Attorney, Agent, or Firm* — Muncy, Geissler, Olds & Lowe, P.C.

(57) ABSTRACT

A lower limb spasticity measurement method includes the step of setting the lower limbs of the person in a lower limb orthotic device of a gait activity machine, the step of starting up a motor of the gait activity machine to drive the lower limb orthotic device for lower limb activity, the step of getting a statistical distribution data from the output torque of the motor within a predetermined time and then calculating the statistical distribution data to obtain a threshold, and the step of determining whether the output torque of the motor is greater than the threshold or not, and then stopping motor if the output torque of the motor is greater than the threshold. Thus, the method of the invention can accurately measures spasticity in the lower limbs of a person without the use of sensors, effectively saving the cost of equipment.

4 Claims, 5 Drawing Sheets

(52) U.S. Cl.
CPC .......... *A61B 5/1124* (2013.01); *A61B 5/7225* (2013.01); *A61B 5/6812* (2013.01)

(58) Field of Classification Search
CPC .... A61H 2201/1676; A61H 2201/1671; A61H 2201/5058–5069; A61H 2201/5079; A61H 2201/5084; A61H 2203/04; A61H 2203/0406; A61H 2205/10–12; A61H 2230/62; A61H 2230/625; A61B 5/224; A61B 5/4571; A61B 5/4585; A61B 5/4595; A61B 5/6811; A61B 5/6812; A61B 5/112; A61B 5/702
USPC ...................................... 601/5; 600/587, 595
See application file for complete search history.

(56) References Cited

U.S. PATENT DOCUMENTS

| | | | | |
|---|---|---|---|---|
| 6,666,831 | B1* | 12/2003 | Edgerton | A61H 1/0237 600/587 |
| 7,163,492 | B1* | 1/2007 | Sotiriades | A61H 1/0237 482/51 |
| 8,308,618 | B2* | 11/2012 | Bayerlein | A61H 1/0237 482/54 |
| 8,460,162 | B2* | 6/2013 | Park | A61H 1/0262 482/1 |
| 8,771,208 | B2* | 7/2014 | Agrawal | A61H 1/024 601/35 |
| 8,920,347 | B2* | 12/2014 | Bayerlein | A63B 22/0235 601/35 |
| 9,314,393 | B2* | 4/2016 | Kim | A61H 1/0255 |
| 9,555,276 | B2* | 1/2017 | Kim | A63B 69/0064 |
| 9,616,282 | B2* | 4/2017 | Tholkes | A63B 22/0664 |
| 9,750,978 | B2* | 9/2017 | Nakashima | A63B 69/0028 |
| 9,895,282 | B2* | 2/2018 | Butters | A61H 3/008 |
| 2008/0312549 | A1* | 12/2008 | Levin | A61B 5/0488 600/546 |
| 2014/0343459 | A1* | 11/2014 | Chino | A61B 5/6829 600/592 |
| 2015/0374278 | A1* | 12/2015 | Hsieh | A61B 5/486 482/8 |
| 2017/0157396 | A1* | 6/2017 | Dixon | A61N 1/36003 |
| 2017/0311848 | A1* | 11/2017 | Wu | A61B 5/11 |

OTHER PUBLICATIONS

MyMedicNews, "Hiwin . . . the Robotic Gait Training System" Video published Sep. 9, 2014. Retrieved from <http://mymedicnews.com/video/756-hiwin-heralds-robotic-age-for-occupational-therapy-and-post-injury-motor-function-recove> on Jun. 22, 2018.*

Schmidt, Henning, et al. "Gait rehabilitation machines based on programmable footplates." Journal of neuroengineering and rehabilitation 4.1 (2007): 2.*

TaiwanTrade.com "Hiwin robotic rehabilitation system to gain China market approval" Mar. 20, 2015. Retrieved from <https://www.taiwantrade.com/news/hiwin-robotic-rehabilitation-system-to-gain-china-market-approval-49247.html#> on Jun. 22, 2018.*

Woodway. "LokoHelp the Way to Walk" May 5, 2015. Retrieved from <https://web.archive.org/web/20150505205651/http://www.woodway.com/products/lokohelp 1/> on Jun. 22, 2018.*

Banala, et al. "Active Leg Exoskeleton (ALEX) for gait rehabilitation of motor-impaired patients." Rehabilitation Robotics, 2007. ICORR 2007. IEEE 10th International Conference on. IEEE, 2007.*

MedGagdet.com "Touring Taiwan's Medtech Sector: Hiwin Enters Medical Space" May 11, 2015. Retrieved from <https://www.medgadget.com/2015/05/touring-taiwans-medtech-sector-hiwin-enters-medical-space.html> on Jun. 22, 2018.* buyKorea.com "Walkbot Robot—assisted gait training system" Oct. 21, 2014. Retrieved from <http://www.buykorea.org/product-details/walkbot-robot-assisted-gait-training-system--3007930.html> Jun. 22, 2018.*

* cited by examiner

LOWER LIMB SPASTICITY MEASUREMENT METHOD

BACKGROUND OF THE INVENTION

1. Field of the Invention

The present invention relates to lower limb activity technologies and more particularly, to a lower limb spasticity measurement method for measuring the spasticity of the lower limbs.

2. Description of the Related Art

For the person with paraplegia caused by spinal cord injury, stroke, nerve damage and other causes . . . , their body positioning, joint movement and other daily activities need to rely on medical aids, further, the implementation of activity works should also be carried out subject to the assistance of related auxiliary devices. However, during the implementation of a activity work, cramps in the lower body of the person can occur due to muscle fatigue or other factors. At this time, the activity work must be stopped, and the activity work can be started again only after the person has enough rest.

US Patent Number 2014/0343459 discloses a spasticity measurement apparatus, which uses a strain gauge and a potentiometer to measure a muscular contraction force for easily evaluating spasticity of the lower limbs. Further, US Patent Number 2008/0312549 teaches a method for quantitative measurement of spasticity in a person by measuring a joint angle and EMG activity in the limb, determining a threshold EMG activity value and a zero angle, recording angle and velocity as a data point at which the measured EMG value crosses the threshold EMG activity value. However, the aforesaid two prior art patents require the use of sensor means to achieve the expected effect, leading to the problem of expensive equipment.

SUMMARY OF THE INVENTION

The present invention has been accomplished under the circumstances in view. It is the main object of the present invention to provide a lower limb spasticity measurement method for measurement of spasticity in the lower limbs of a person, which directly fetches motor torque signal for measurement of spasticity without the use of additional sensors, thereby effectively saving equipment cost.

To achieve this and other objects of the present invention, a lower limb spasticity measurement method comprises a first step of letting a person enter a gait activity machine and then setting the lower limbs of the person in a lower limb orthotic device of the gait activity machine, a second step of starting up a motor of the gait activity machine to drive the lower limb orthotic device in assisting activity of the lower limbs of the person, a third step of getting a statistical distribution data from the torque output of the motor within a predetermined time and then calculating the statistical distribution data to obtain a threshold, and a fourth step, namely, the last step of determining whether the output torque of the motor is greater than the threshold or not. If the output torque is greater than the threshold, it means that the person gets spasticity. At this time, stop the motor immediately. If the output torque is not greater than the threshold, it means the condition of the person is normal. At this time, let the motor keep running.

Further, the statistical distribution data is divided into a positive half cycle interval and a negative half cycle interval. The threshold for the positive half cycle interval and the threshold for the negative half cycle interval are defined as $TH^{up} = \mu^{up} \pm 3\sigma^{up}$ and $TH^{down} = \mu^{down} \pm 3\sigma^{down}$ respectively, in which $TH^{up}$ is the threshold of the positive half cycle interval; $\mu^{up}$ is the mean value of the positive half cycle interval; $\sigma^{up}$ is the standard deviation of the positive half cycle interval; $TH^{down}$ is the threshold of the negative half cycle interval; $\mu^{down}$ is the mean value of the negative half cycle interval; $\sigma^{down}$ is the standard deviation of the negative half cycle interval.

Further, in lines with the needs of different people, the aforesaid two equations can be modified subject to the operating speed of the motor, the stride length of the person and the sensitivity of the gait activity machine to Other advantages and features of the present invention will be fully understood by reference to the following specification in conjunction with the accompanying drawings, in which like reference signs denote like components of structure.

DETAILED DESCRIPTION OF THE INVENTION

Figure 1:
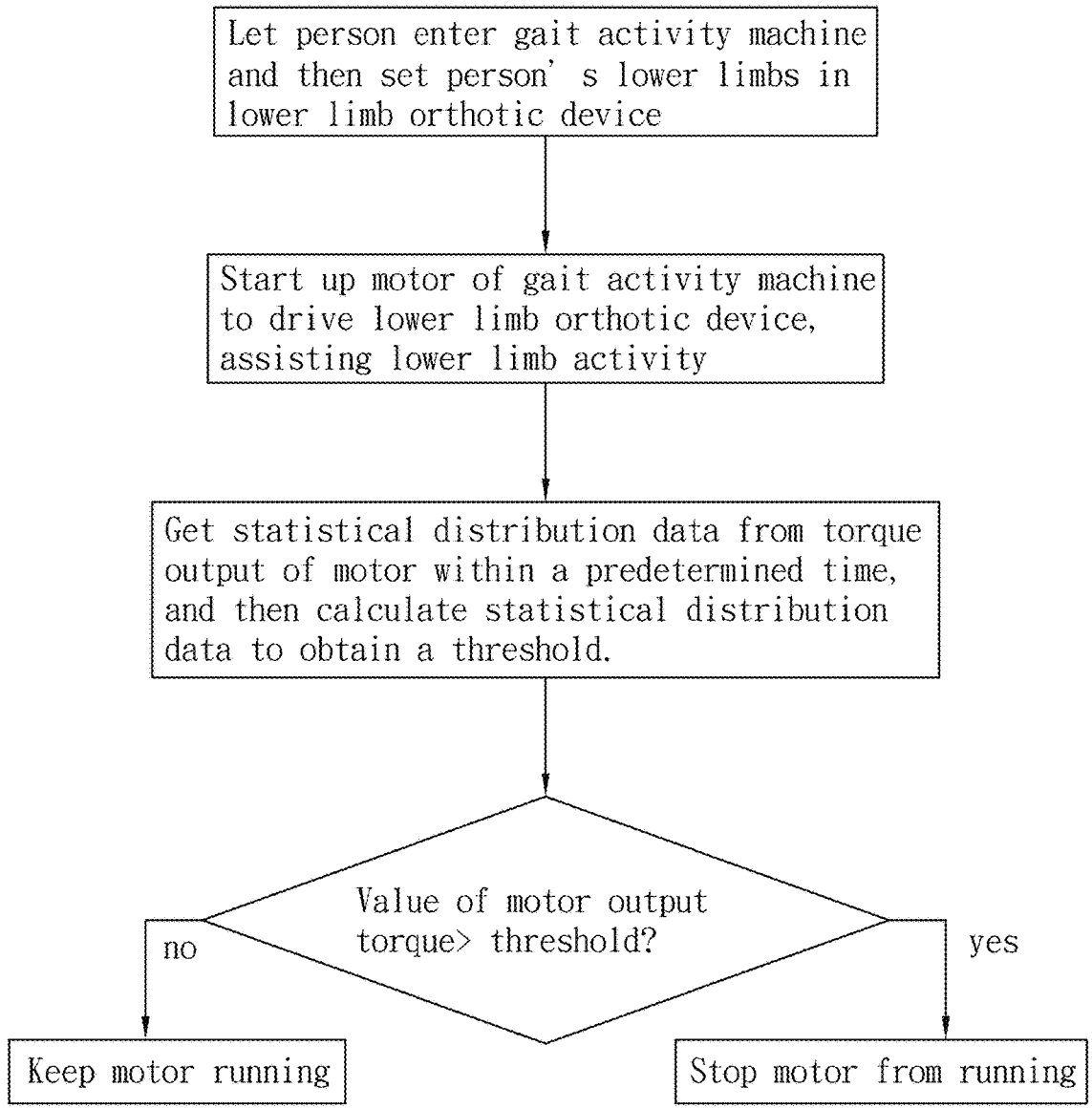
FIG. 1 is a flow chart of a lower limb spasticity measurement method in accordance with the present invention.
Figure 2:
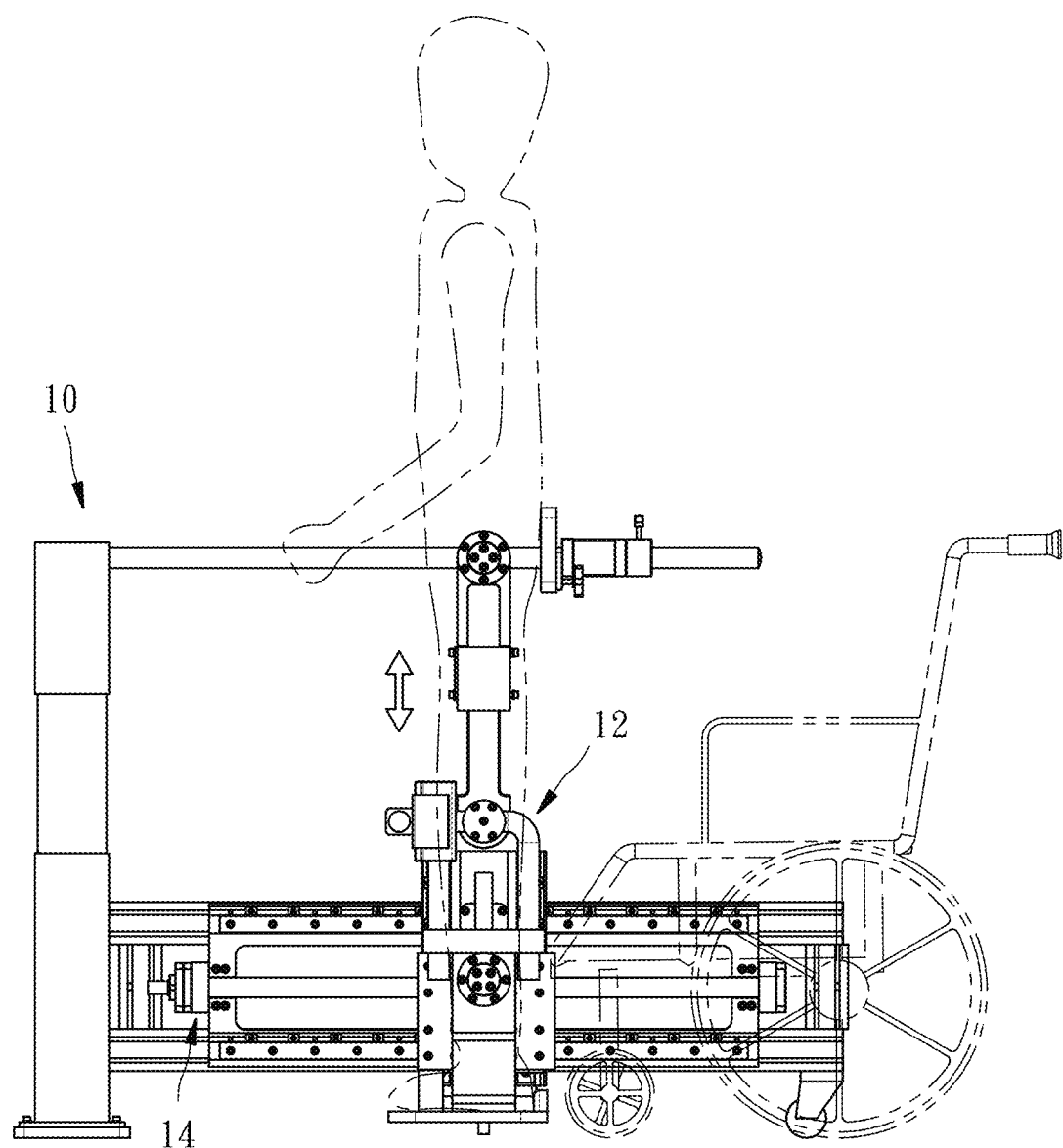
FIG. 2 is a schematic structural view of a gait activity machine used in accordance with the present invention.

Referring to FIG. 1, a lower limb spasticity measurement method in accordance with the present invention comprises the steps as follows:

a) Let a person enter a gait activity machine 10, as illustrated in FIG. 2, and then set the lower limbs of the person in a lower limb orthotic device 12.

b) Start up a motor 14 of the gait activity machine 10 to drive the lower limb orthotic device 12, assisting activity of the lower limbs of the person.

c) Get a statistical distribution data from the output of the torque variation of the motor 14 within a predetermined time, and then calculate the statistical distribution data to obtain a threshold.

Figure 3:
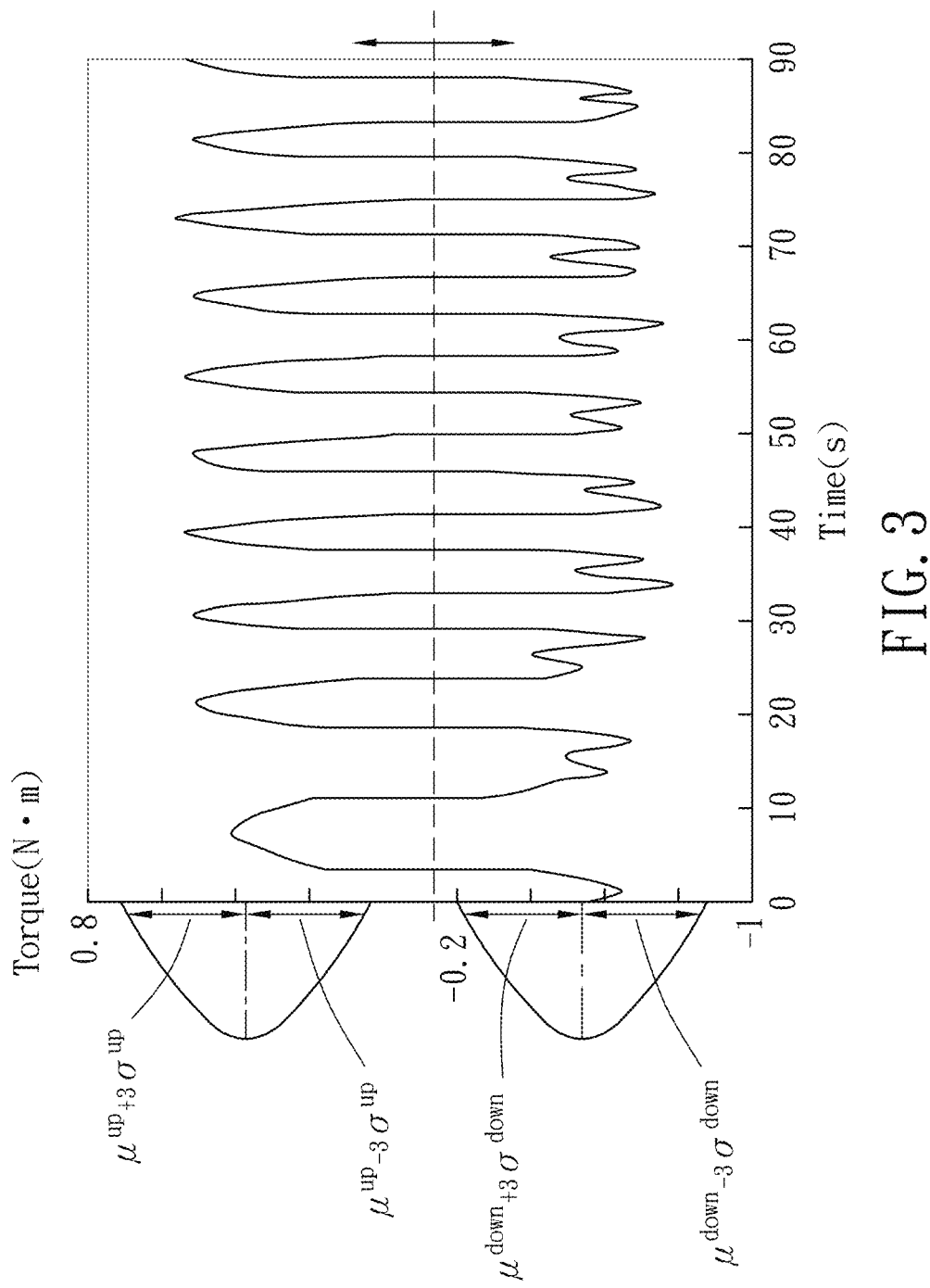
FIG. 3 is a scatter plot of motor torque versus time graph coordinates.
Figure 4:
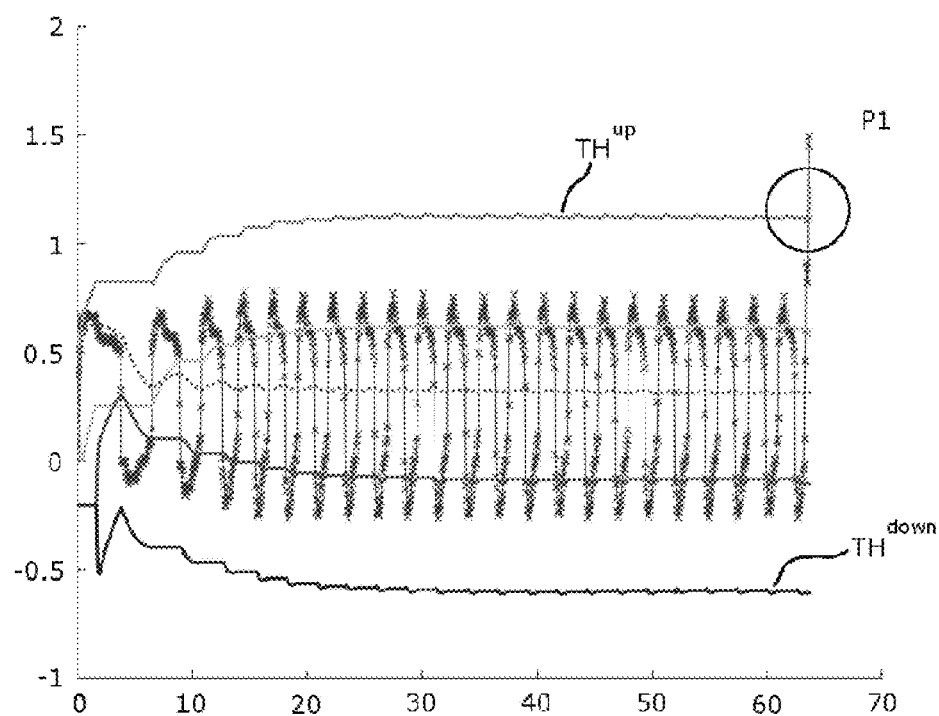
FIG. 4 is similar to FIG. 3, illustrating spasticity occurred in the lower limbs of the person.

As illustrated in FIG. 3, the statistical distribution data is divided into a positive half cycle interval and a negative half cycle interval. The projection of the positive half cycle interval and the projection of the negative half cycle interval on y-axis respectively form a normal distribution. A normal signal will fall within this normal distribution. Thereafter, use the concept of confidence interval to determine the data of one particular measurement point to be or not to be a normal signal. If the data of this particular measurement point is a normal signal, the data of this particular measurement point will fall within the range of the mean value of the positive, negative half cycle interval plus or minus three standard deviations. Therefore, in this step c), calculate the mean value and standard deviation of the positive and negative half cycle intervals, and then define the threshold for the positive and negative half cycle intervals using the concept of confidence interval, and thus, the following two equations are obtained:

$$TH^{up}=\mu^{up}\pm 3\sigma^{up}$$

$$TH^{down}=\mu^{down}\pm 3\sigma^{down}$$

in which $TH^{up}$ is the threshold of the positive half cycle interval; $\mu^{up}$ is the mean value of the positive half cycle interval; $\sigma^{up}$ is the standard deviation of the positive half cycle interval; $TH^{down}$ is the threshold of the negative half cycle interval; $\mu^{down}$ is the mean value of the negative half cycle interval; $\sigma^{down}$ is the standard deviation of the negative half cycle interval.

d) Determine whether or not the output torque of the motor 14 is greater than the threshold? If the output torque is greater than the threshold, as indicated by P1 in FIG. 4, it means that the person gets spasticity. At this time, stop the motor 14 immediately. If the output torque is not greater than the threshold, it means the condition of the person is normal. At this time, let the motor 14 keep running.

Figure 5:
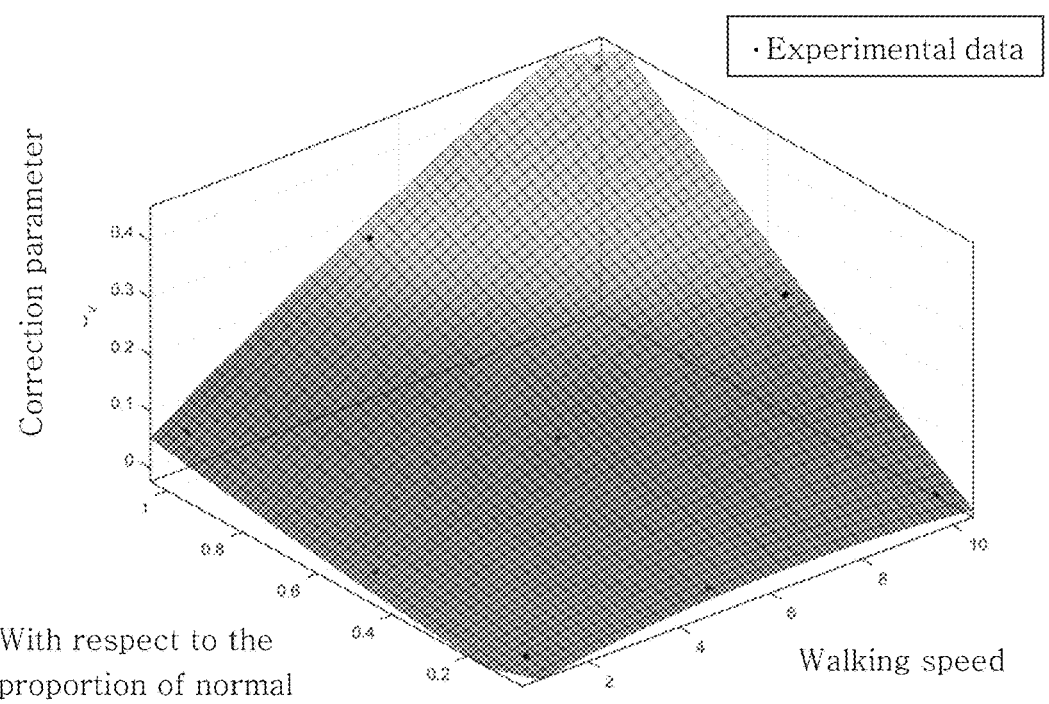
FIG. 5 is a plot illustrating the surface correction of the correction parameter.
Figure 6:
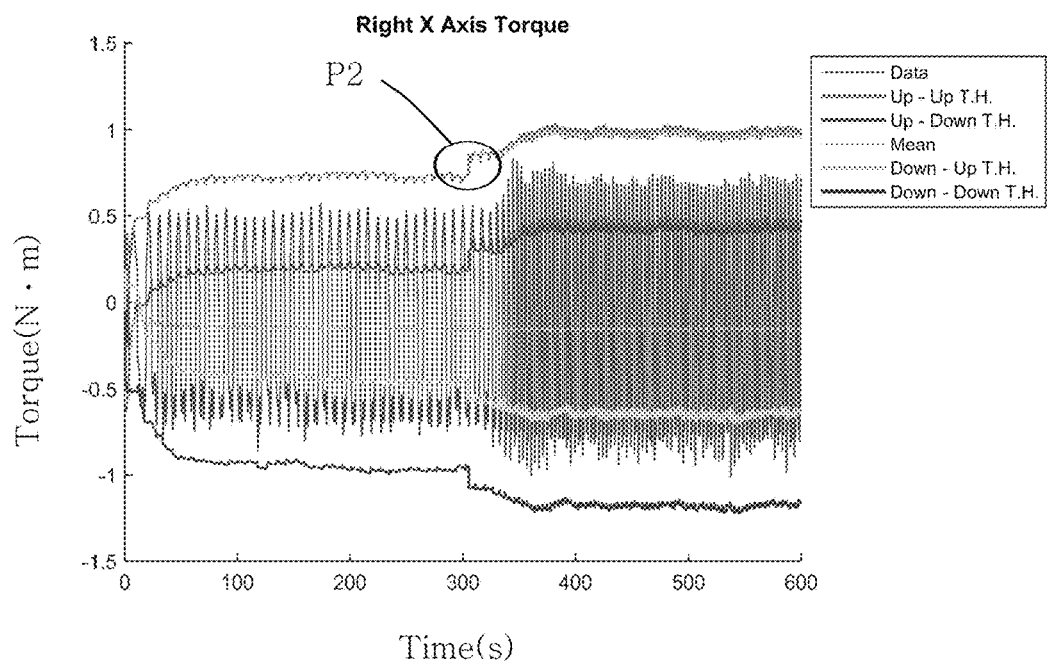
FIG. 6 is a scatter plot of motor torque versus time graph coordinates obtained after added correction parameter to the threshold.

On the other hand, since stride length varies widely from patient to patient and the operating speed of the motor 14 may also be differently set for different people, the present invention utilizes surface fitting technique to calculate the operating speed of the motor 14 and the stride length of the person so as to obtain a correction parameter (see FIG. 5). Thus, the threshold of the positive half cycle interval is corrected to become $TH^{up}=\mu^{up}\pm 3\sigma^{up}+Sv$ for the positive half cycle interval and $TH^{down}=\mu^{down}\pm 3\sigma^{down}-Sv$ for the negative half cycle interval, in which Sv is the correction parameter. Therefore, it can be seen from P2 in FIG. 6, it is assumed to change the operating speed of the motor 14 in the first 300 seconds, the threshold will be automatically corrected without needing recalibration.

Figure 7:
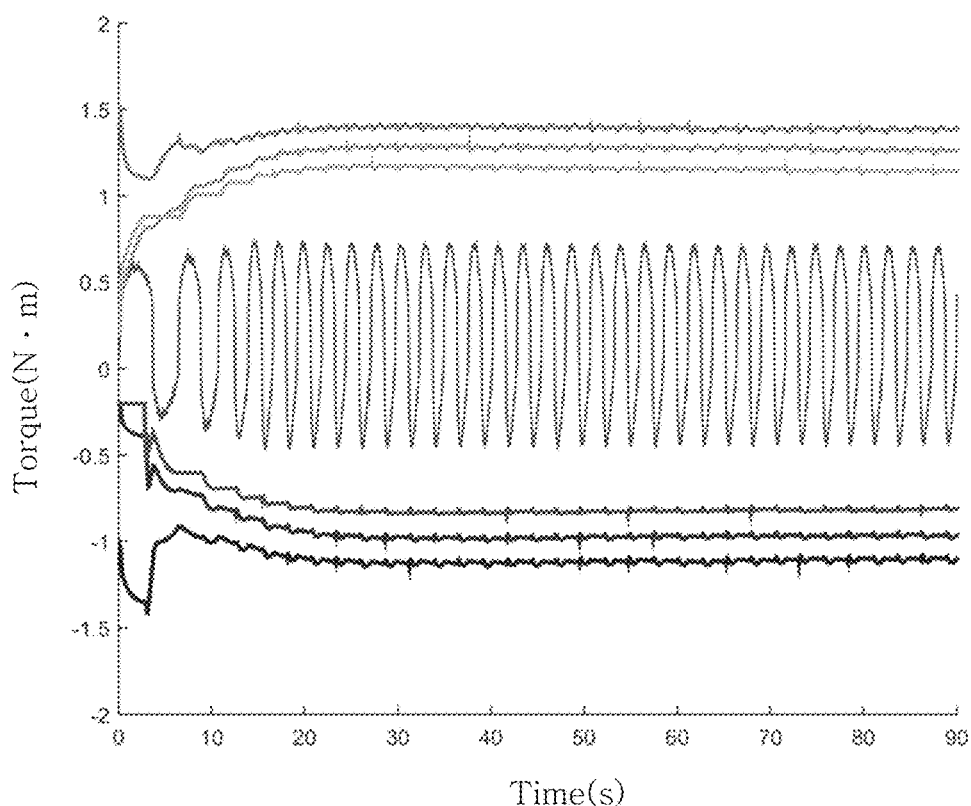
FIG. 7 is a scatter plot of motor torque versus time graph coordinates obtained after added sensitivity parameter to the threshold.

Further, a sensitivity parameter can be added to the equation, enabling the threshold to be further corrected to become $TH^{up}=\mu^{up}\pm 3\sigma^{up}+Sv+S\omega^{up}$ for the positive half cycle interval and $TH^{down}=\mu^{down}\pm 3\sigma^{down}-Sv+S\omega^{down}$ for the negative half cycle interval, in which $S\omega^{up}$ and $S\omega^{down}$ are the sensitivity parameter for the gait activity machine in spasticity measurement. This sensitivity parameter satisfies the following equations:

$$S\omega^{up}=(\mu^{up}-\mu^{data})*\omega$$

$$S\omega^{down}=(\mu^{data}-\mu^{down})*\omega$$

in which $\mu^{data}$ is the overall mean value of the statistical distribution data; $\omega$ is the weight in the range from the most sensitive 0 to the least sensitive 1. With this sensitivity parameter, it allows adjustment of the range of the threshold according to the condition of the person, as illustrated in FIG. 7, thus achieving the effect of changing the sensitivity of the measurement.

In conclusion, the lower limb spasticity measurement method of the invention utilizes the output torque of the motor 14 as signal source for measuring spasticity in the lower limbs of a person during activity without the use of additional sensors. Thus, the method of the invention effectively saves the cost of equipment. Further, during activity, the person can adjust the speed without re-calibration, and can also adjust the sensitivity of the measurement according to the person's personal needs, thereby enhancing the ease of use.

What is claimed is:

1. A lower limb spasticity measurement method without a sensor, comprising the steps:
   a) letting a person enter a gait activity machine, and then setting the lower limbs of said person in a lower limb orthotic device of said gait activity machine;
   b) starting up a motor of said gait activity machine to drive said lower limb orthotic device for the activity of the lower limbs of said person;
   c) getting a statistical distribution data from an output of a torque variation of said motor within a predetermined time, and then calculating said statistical distribution data to obtain a threshold; and
   d) spasticity is determined if the output torque is greater than the threshold, stopping said motor if the output torque of said motor is greater than said threshold;
   wherein the statistical distribution data comprises a positive half cycle interval and a negative half cycle interval,
   the threshold for the positive half cycle intervals and the threshold for the negative half cycle intervals are defined as:

$$TH^{up}=\mu^{up}\pm 3\sigma^{up}$$

$$TH^{down}=\mu^{down}\pm 3\sigma^{down}$$

wherein $TH^{up}$ is the threshold of the positive half cycle interval; $\mu^{up}$ is a mean value of the positive half cycle interval; $\sigma^{up}$ is a standard deviation of the positive half cycle interval; $TH^{down}$ is the threshold of the negative half cycle interval; $\mu^{down}$ is a mean value of the negative half cycle interval; $\sigma^{down}$ is a standard deviation of the negative half cycle interval.

2. The lower limb spasticity measurement method as claimed in claim 1, wherein the threshold for said positive half cycle interval and the threshold for said negative half cycle interval are further defined as $TH^{up}=\mu^{up}\pm 3\sigma^{up}+Sv$ and $TH^{down}-\mu^{down}\pm 3\sigma^{down}$ Sv respectively, in which Sv is a correction parameter that is obtained by calculating the operating speed of said motor and the stride length of said person using surface fitting technique.

3. The lower limb spasticity measurement method as claimed in claim 2, wherein the threshold for said positive half cycle interval and the threshold for said negative half cycle interval are further defined as $TH^{up}=\mu^{up}\pm 3\sigma^{up}+Sv+S\omega^{up}$ and $TH^{down}=\mu^{down}\pm 3\sigma^{down}$ $SV+S\omega^{down}$ respectively, in which $S\omega^{up}$ and $S\omega^{down}$ are the sensitivity parameter for the gait activity machine in spasticity measurement.

4. The lower limb spasticity measurement method as claimed in claim 3, wherein said sensitivity parameter satisfies the equation of $S\omega^{up}=(\mu^{up}-\mu^{data})*\omega$ and the equation of $S\omega^{down}=(\mu^{data}-\mu^{down})*\omega$, in which $\mu^{data}$ is the overall mean value of the statistical distribution data; $\omega$ is the weight in the range from the most sensitive 0 to the least sensitive 1.

* * * * *